United States Patent

Valentin

[11] Patent Number: 5,951,164
[45] Date of Patent: Sep. 14, 1999

[54] METHOD FOR CONTACTLESS CONTINUOUS TEMPERATURE MEASUREMENT OF THE SOLIDIFICATION OF METAL ALLOYS

[75] Inventor: Rudolf Valentin, Ronneby, Sweden

[73] Assignee: Novacast Aktiebolag, Ronneby, Sweden

[21] Appl. No.: 08/983,302
[22] PCT Filed: Jun. 30, 1995
[86] PCT No.: PCT/SE95/00811
  § 371 Date: Dec. 30, 1997
  § 102(e) Date: Dec. 30, 1997
[87] PCT Pub. No.: WO97/02485
  PCT Pub. Date: Jan. 23, 1997
[51] Int. Cl.[6] .................... G01K 1/08
[52] U.S. Cl. ............ 374/153; 374/120; 374/139
[58] Field of Search .................... 374/120, 121, 374/124, 137, 139–143, 153–154

[56] References Cited

U.S. PATENT DOCUMENTS 4,877,331  10/1989  Schrors .................... 374/153

FOREIGN PATENT DOCUMENTS 385 600   4/1988   Australia .

OTHER PUBLICATIONS

Derwent's abstract, No. 19612 B/10, Week 7910 Abstract of SU, 602838 (Moscow Steel Alloys Inst), Mar. 28, 1978.

Derwent's abstract, No. 92–267296/32, Week 9232, Abstract of SU, 1689769 (Mosc Steel Alloys Inst), Nov. 7, 1991.

*Primary Examiner*—Vit Miska
*Attorney, Agent, or Firm*—Pillsbury Madison & Sutro LLP

[57] ABSTRACT

A method for contactless continuous temperature measurement of the solidification of metal alloys is described, according to which the melt to be analysed is rotated about a vertical axis in a cylindrical and concentrically positioned test piece (2), and the temperature measurement is effected with the aid of an optical temperature meter (6). Upon rotation, a parabola-shaped inner surface forms, and the temperature measurement is performed on a part of the upper interface of the parabola.

5 Claims, 2 Drawing Sheets

METHOD FOR CONTACTLESS CONTINUOUS TEMPERATURE MEASUREMENT OF THE SOLIDIFICATION OF METAL ALLOYS

The present invention concerns a method for contactless continuous temperature measurement of the solidification of metal alloys.

Metal alloys consist of a base metal alloyed with one or several chemical elements. Examples of alloys are bronze, brass and cast iron. During the solidification the various phases are separated from the melt until the latter has been transformed entirely into its solid phase. Phase separation liberates melting heat. The melting heat temporarily slows down the rate of solidification. By adding replenishing melt to a test piece it becomes possible to observe the solidification process by means of a thermocouple and to study the temperature-time progress. A melt having a specific chemical composition may solidify in various ways, depending on its contents of gases and nucleating agents. The manner in which the alloy solidifies affects its castability and its physical characteristics. During the last 20 years studies of the temperature-time diagram have been used in industry to analyse metal melts. As a result of these studies it has become possible to identify characteristic properties as the solidification progresses, characteristics which may be correlated to specific properties of the alloy. The method is known as thermal analysis and is used to make it possible to predict the properties of various alloys and thus to control the complex melting and treatment processes connected with different alloys.

Thermal analysis is most widely used in connection with cast-iron alloys. Thermal analysis permits more efficient process control, with resulting considerable savings in the foundry in the form of less scrapping, higher product yield and lower consumption of inoculants and other additives. Cast iron alloys are based on iron alloyed with carbon, silicon, phosphor and often also manganese, chromium, copper and other substances. In the thermal analysis operation a test piece is cast, which is manufactured from so called shell sand and provided at its centre with a thermocouple of platinum/platinum-rhodium. The module of the test piece is approximately 0.75 cm, equivalent to a solidification time of about 2.5 minutes to reach the solidus temperature of the alloy. The test piece can only be used once, since the thermocouple becomes embedded in the test piece during the casting and the heat degrades the bonding agent in the test piece mould. In order to study the melting process at least one test per melt is required. The consumption of test pieces therefore may become considerable and is a serious cost-increasing factor. Since the thermocouples are of a disposable nature, repeatable measurement accuracy may be uncertain.

An obvious line of action has been to attempt to use optic temperature-measuring instruments (pyrometers) for contactless sensing of the temperature by performing measurements on the surface of a test piece. Optical pyrometers are based on measurement of the radiation within the infra-red range. The radiation depends on the surface temperature of the object and on its emissivity. The problem is that the emissivity varies during the solidification. For instance, as cast iron solidifies endogenous slag formation occurs when the temperature is below the so called equilibrium temperature of the melt. As soon as the temperature is lower than the equilibrium temperature silicon and manganese, for instance, oxidise, forming slags. The density of the slags is about 2.5 as compared to about 6.9 in the case of the melt, for which reason the slag remains on the surface. Thus, the slags change the emissivity in a manner that is difficult to predict. The use of optic temperature-measuring methods in the case of thermal analysis, requiring constant surveillance of the temperature, from the casting temperature to that of solidus, therefore hitherto has been prohibited, since this method has failed to produce the required measurement accuracy.

The object of the present invention is to allow the use of optical temperature measurement for contactless continuous measurement of the progress of solidification of metal alloys. Thus, the invention makes it possible to considerably reduce the costs of test pieces having built-in thermocouples.

The invention thus concerns a method for contactless temperature measurement of the solidification of metal alloys, comprising rotating the melt to be analysed about a vertical axis in a cylindrical and concentrically positioned test piece, and effecting the temperature measurement with the aid of an optical temperature meter, the method being characterised in that a parabola-shaped inner surface is formed during said rotation and in that the temperature measurement is performed on a part of the upper interface of the parabola.

The invention will be described below in greater detail with reference to the accompanying drawings, wherein.

The melt 3 to be analysed is poured into a test piece 2 which is brought into a rotational movement about a vertical axis 7. During the rotation, the centrifugal force separates the melt from separated slag. The slag, having the lower density, collects at the centre of the parabola-shaped inner surface 4. By adjusting the rotational speed it becomes possible to give the parabola-shaped inner surface the configuration most suitable for the intended purpose. In the upper part of the parabola a concentric zone forms, which is practically free of slag and which has a stable emission suitable for optical temperature measurement. Newly-formed slag is conveyed by the centrifugal force towards the bottom of the parabola surface.

Figure 1:
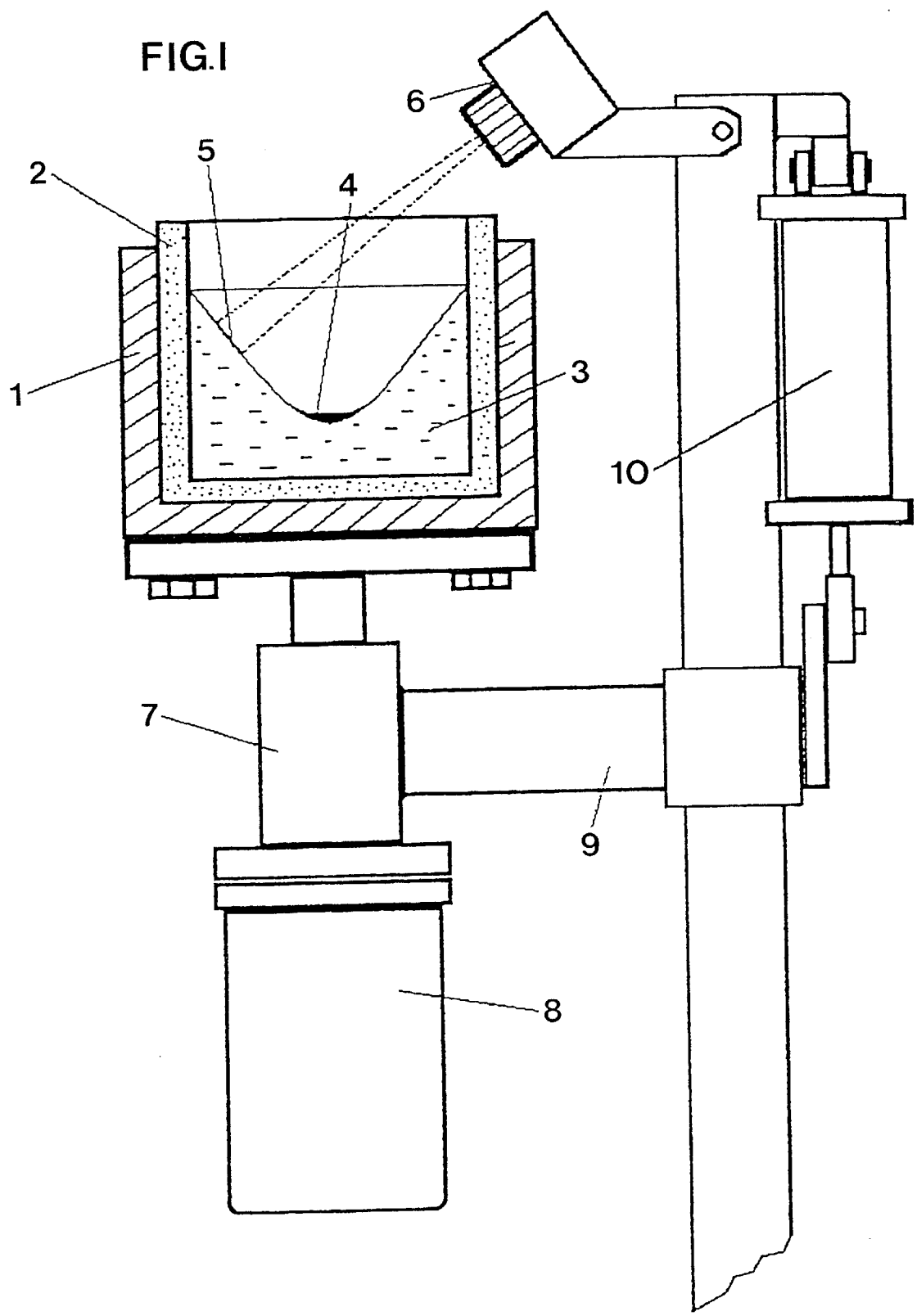
FIG. 1 is a schematical view of a device for performing the method.

In accordance with the embodiment of FIG. 1, the test piece 2 manufactured in shell sand has a wall thickness of about 5 mm and is placed in a cylindrical steel support 1. The test piece 2 is depressed into the support 1 and is retained therein by friction. The support is mounted on a vertical shaft 7 which is directly connected to an electric motor 8. The shaft 7 is connected to a horizontal shaft 9 mounted in a stand connected to a piston cylinder aggregate 10. The upper part of the stand supports an optical pyrometer 6. The optical pyrometer preferably is spaced about 500 mm from the surface 5 to be tested. The optics of the pyrometer is adapted to give a diameter of the surface 5 to be tested of preferably about 5 mm. Several suitable kinds of optical pyrometers are available on the market. The pyrometer 6 may be of two-colour type or be arranged to measure only a limited part of the spectrum in order to minimise the effects of varying emission coefficients. Preferably, the pyrometer is set to ensure that the registered temperatures are integrated mean values measured over a time period of preferably 1 s.

Preferably, the diameter of the test piece is chosen within the range of 80–150 mm and its height within the range of 80–100 mm. The rotational speed is adjusted to the diameter and so as to ensure that the desired parabola configuration producing satisfactory slag separation is achieved. In accordance with one embodiment according to which the inner diameter size is 100 mm and the height 80 mm, a rotational speed of 150 rpm was found to be suitable to produce a parabola surface in which the vertical difference between the upper and the lower levels was about 40 mm. Under these diameter and rotational speed conditions a solidification module of about 0.75 cm was obtained, i.e. the same as in a traditional test piece.

Figure 2:
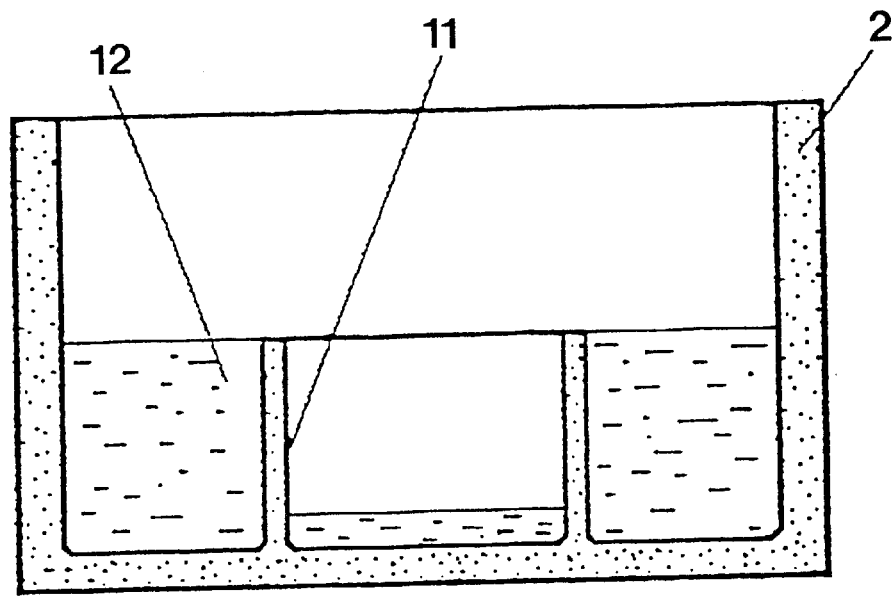
FIG. 2 illustrates a sampling ladle in position of rest.
Figure 3:
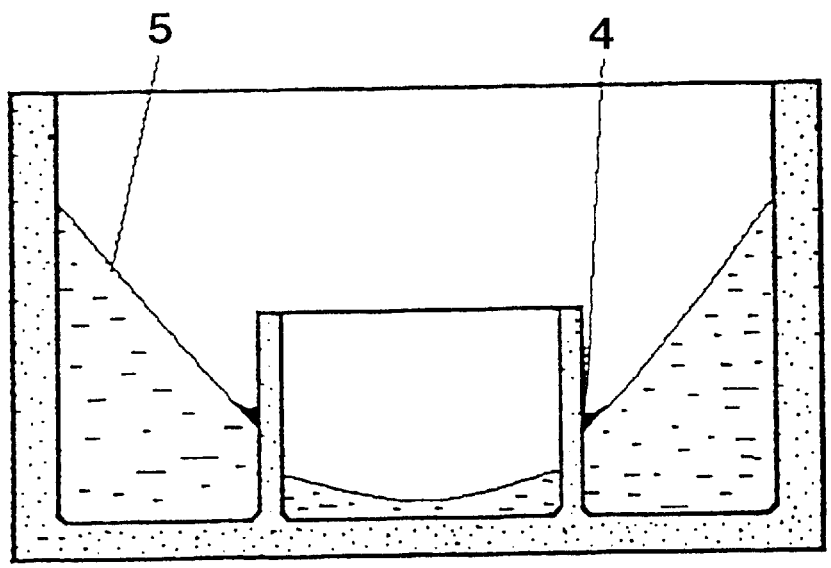
FIG. 3 illustrates the same ladle during its rotation.

In order to ensure that the measurement surface assumes the same position during repeated analyses, it is essential that the melt volume is constant. This may be achieved by using a sampling ladle which is always filled to a predetermined level, or by weighing. According to the invention the problem may be solved by providing the test piece 2 with an interior concentric cylinder 11 in accordance with FIG. 2. The height of the inner cylinder is chosen to correspond to the desired level of the melt 12 in the test piece. Melt is replenished into the outer cylindrical space 12 of the test piece without rotation of the latter, until overflow occurs and melt enters into the centrally positioned space (FIG. 2). The test piece is then rotated, causing the slag to be attracted towards the inner surface 4 (FIG. 3).

In accordance with the previously described embodiment a suitable size of the inner cylinder is an external diameter of about 30 mm, a height of about 50 mm and a wall thickness of 5 mm.

When the measurement is completed, i.e. when the solidus temperature has been reached and the sample has solidified, the measurement is interrupted and the rotational motion is stopped. The aggregate 10 is then activated to turn the shaft 9 over approximately 170°, causing the test piece to fall out. After purging the support 1, the latter is turned back to its original position and a new test piece is introduced into the support 1. The device is then ready for a new measurement operation.

In the case of certain alloys that are extremely sensitive to oxidation it may be necessary to add protective gases in the parabola-shaped space. Suitable protective gases are argon, nitrogen and in some cases carbon dioxide.

In some cases it may be desirable to add inoculants or other additives to the melt in order to affect the solidification process. In accordance with the invention the additives may be supplied to the melt in the test piece. The rotational movement ensures homogeneous mixing of the additive.

The invention makes it possible to measure the temperature-time progress during the solidification at two or several solidification speeds with respect to one and the same sample. This is achieved by adaptation of the parabola surface shape with the aid of the rotational speed and/or the shape of the inner surface of the test piece. At the upper part of the parabola surface the ratio volume/area is smaller than in the lower part thereof. By simultaneously measuring at two different levels of the parabola surface it thus becomes possible to study the solidification progress at different solidification speeds. The shape could also be adjusted to produce different solidification times, e.g. by forming the inner surface of the test piece with concentric annular depressions at different vertical levels.

In summary, the subject invention provides the following advantages compared with the prior-art technology, viz.:

1. Provision of a measurement face practically void of slag.
2. Possibility to vary the solidification time by altering the parabola shape.
3. Production of a certain mixing and homogenisation effect.
4. Integrated measurement value produced by the rotating surface.
5. Convenient application of a protective gas in the parabola cavity.
6. Possibility to measure at two points having different solidification modules.
7. Low variable costs per measurement operation.

I claim:

1. A method for contactless continuous temperature measurement of the solidification of metal alloys, comprising the steps of rotating the melt to be analysed about a vertical axis in a cylindrical and concentrically positioned test piece (2), and effecting the temperature measurement with the aid of an optical temperature meter (6), characterised in that a parabola-shaped inner surface is formed during said rotation, and in that the temperature measurement is performed on a part of the upper interface (5) of the parabola.

2. A method as claimed in claim 1, characterised in that the test piece consists of a circular mould (2), preferably formed from core sand or other suitable material and including an inner concentrically positioned cylinder (11), the height of which coincides with the desired height of the melt contained in the outer part of the test piece.

3. A method as claimed in claim 1, characterised by carrying out the temperature measurement simultaneously at two different vertical levels in the parabola, and by forming the parabola in such a manner by means of the rotational speed that said levels correspond to different solidification times.

4. A method as claimed in claim 3, characterised by varying the solidification time in the test piece by means of concentric rings, said rings formed on the inner test piece surface at various levels and having different depths.

5. A method as claimed in claim 1, characterised by adding a protective gas, preferably argon, nitrogen or carbon dioxide to the parabola-shaped cavity (4) to displace all oxygen.

* * * * *

UNITED STATES PATENT AND TRADEMARK OFFICE
CERTIFICATE OF CORRECTION

PATENT NO. : 5,951,164

DATED : September 14, 1999

INVENTOR(S) : SILLEN

It is certified that error appears in the above-identified patent and that said Letters Patent is hereby corrected as shown below:

On the title page, items:

[19] Change "Valentin" to --Sillen--.

[75] Change "Rudolf Valentin" to --Rudolf Valentin Sillen--.

Signed and Sealed this

Eighteenth Day of April, 2000

Attest:

Q. TODD DICKINSON

*Attesting Officer*  *Director of Patents and Trademarks*